United States Patent [19]

Reeves

[11] Patent Number: 5,135,470
[45] Date of Patent: Aug. 4, 1992

[54] SHOULDER AND BACK SUPPORT BRACE

[76] Inventor: Bryan Reeves, 43 Liberty Parade, West Ivanhoe, Victoria 3079, Australia

[21] Appl. No.: 793,278

[22] Filed: Nov. 12, 1991

Related U.S. Application Data

[63] Continuation of Ser. No. 401,974, Sep. 1, 1989, abandoned.

[51] Int. Cl.[5] ............................................. A61F 5/02
[52] U.S. Cl. ........................................ 602/19; 2/44
[58] Field of Search .............. 602/19; 128/99.1, 101.1, 128/102.1; 2/44, 45; 606/241

[56] References Cited

U.S. PATENT DOCUMENTS

| | | | |
|---|---|---|---|
| 369,803 | 9/1887 | McComber | 128/78 |
| 496,816 | 5/1893 | Corker | 128/78 |
| 4,541,419 | 9/1985 | Osawa | 128/78 |

FOREIGN PATENT DOCUMENTS

| | | |
|---|---|---|
| 13902/70 | 4/1079 | Australia . |
| 569318 | 1/1924 | France ............................... 128/102.1 |
| 2159058 | 11/1986 | United Kingdom . |

OTHER PUBLICATIONS

Allen & Hanburys Ltd. London, Brochure.

Primary Examiner—Richard J. Apley
Assistant Examiner—Linda C. Dvorak
Attorney, Agent, or Firm—Andrus, Sceales, Starke & Sawall

[57] ABSTRACT

A back and shoulder brace comprising flexible elastic elements to apply a compliant pressure that holds the shoulders back and places the spine under mild compression. The brace has a waist strap as a principal anchor with an elastic spinal strap joining two shoulder straps.

7 Claims, 6 Drawing Sheets

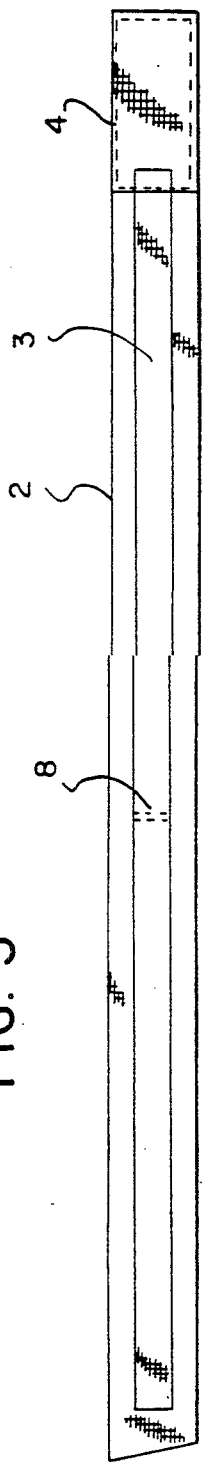
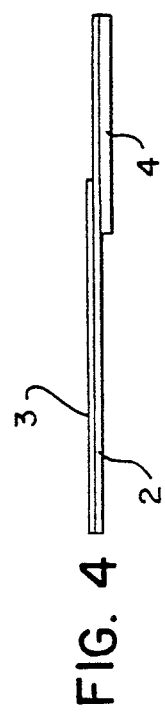
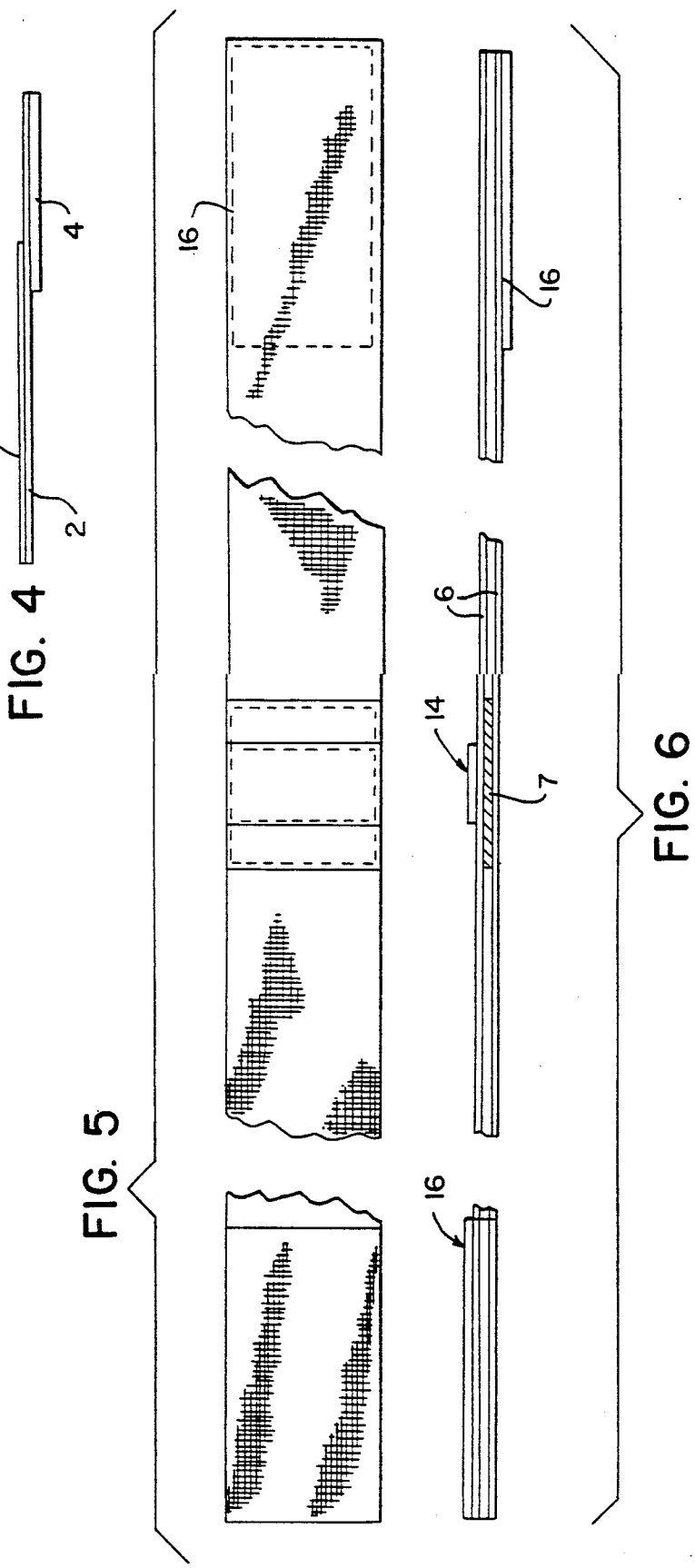
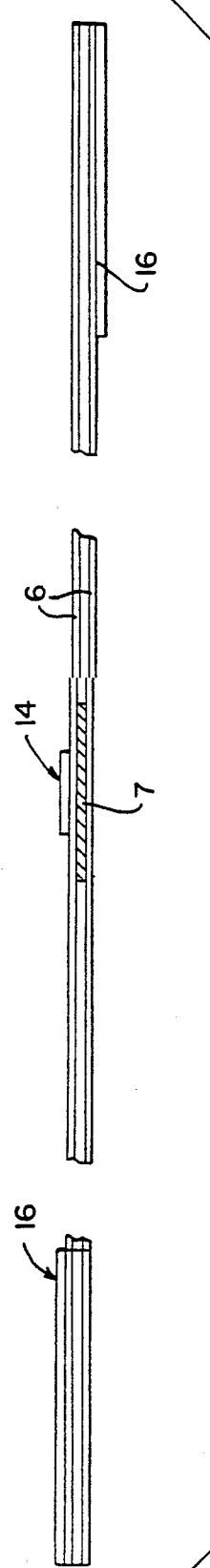
FIG. 3
FIG. 4
FIG. 5
FIG. 6

SHOULDER AND BACK SUPPORT BRACE

The present application is a continuation application of U.S. patent application Ser. No. 07/401,975, filed Sep. 1, 1989, now abandoned.

FIELD OF THE INVENTION

This invention relates to a posture correcting device and in particular to a brace for adjusting the posture of the spine.

BACKGROUND OF THE INVENTION

The human spine is a vertebral column enclosing the spinal cord which consists of 34 bones: 7 cervical, 12 dorsal or thoracic, 5 lumbar, 5 sacral vertebrae forming one bone, the sacrum and 4 coccygeal vertebrae fused to form the coccyx. In a normal orientation the column adopts a particular "S" shaped curve beginning with the concave cervical region extending to the convex dorsal or thoracic region, followed by a concave lumbar region which joins the sacral and coccyx bones to form the lauda equina region.

In a healthy optimum condition, the vertebrae of the spinal column are well placed in relation to each other so as to avoid excessive contact or pressure.

In a diseased, pressured or injured state however, the vertebrae can come into contact with each other or be placed under stress which can result in a number of symptoms including muscular strain, vertebrae misalignment or dislocation, nerve irritation etc, all amounting to one form or another of back problem.

Back injury can result from a wide range of causes. Anything from an actual direct injury, poor posture for a prolonged period of time, poor bending or lifting methods or simply old age where the vertebrae and/or the fibrocartilage intervertebral disks wear can result in injury. In particular wear on the back occurs mainly between the 5th lumbar and sacral vertebrae.

Once the back has been stressed or injured, it is vital to pay particular attention to correcting any deviation from its proper shape and/or to relieve any stress in order to facilitate recovery. If any form of back problem is left unattended for a long period of time, acute or chronic pain and injury can result requiring surgery, traction or other drastic forms of correction.

DESCRIPTION OF THE PRIOR ART

In order to cater for back injury or stress, a large number of back aids are available to assist in correcting and servicing the posture and stress of the back. The types of aids available fall into two broad categories:
  a) Back supports,
  b) Shoulder restraints and supports.

The back supports are either a variety of elastic or other binders which wrap around the stomach or hips to keep the back in shape, or alternatively a variety of hard inflexible braces which incorporate numerous metal strips shaped to the contour of the spinal column and bound around the stomach by straps or bindings. In all of these devices the support given to the spine is local and always in a dorso-ventral or horizontal plane.

The range of shoulder restraints and supports are usually designed with a wide elastic panel at the back with fixed elastic shoulder straps that travel around the arms to keep the shoulders straight. However, these shoulder supports suffer from the same drawbacks as the back supports in that the support given is very local and in a dorso-ventral plane.

At present, there is nothing available that offers a complete vertical support over the whole length of the spinal column whilst allowing the wearer to move freely and without undue constraint.

BRIEF SUMMARY OF THE INVENTION

The object of the present invention is to provide an improved back and shoulder support means.

Accordingly, the invention provides a posture correction and support device comprising a first support means adapted to lie along the spinal column, a second support means connected to the top of said first support means and adapted to fit over the shoulder, under the arm and connect back to said first support means, and a third support means connected to the bottom of said first support means and adapted to fit around the waist.

In a preferred form, the second support means are a matching pair of straps adapted to fit over either shoulder, under the arms and connect together at the thoracic region of the first support means.

Alternatively the pair of second support means may be one continuous elastic strap sewn to the top of the first support means.

Conveniently, the support means are elastic straps with adjustable connection means.

Preferably the first and second support means are about 2" wide and made of elastic strap sewn together at the top to form a "Y" or "T" joint and connecting at the thoracic region by any convenient fastening means such as the material sold under the registered trade mark VELCRO.

The third support means is preferably a 4" elastic strap connected to the first support means by similar fastening means.

Preferably the first support means consist of dual straps of 2" elastic, stretchably laminated. The second support means consists of a 2" and a 1" strap of elastic stretchably laminated and the third support consists of dual straps of 4" elastic stretchably laminated.

Preferably the third support means incorporates a pelvic anchor adapted to pass under the crotch and prevent the third support means from moving up the waist.

Preferably the pelvic anchor comprises two straps of elastic or inelastic material removably connected to the third support means.

BRIEF DESCRIPTION OF DRAWINGS

Other objects, features and advantages of the invention will become apparent from the following description of preferred embodiments and the accompanying drawings, in which:

FIG. 3 is a plan view of the shoulder strap.

FIG. 4 is a cross section of the shoulder strap.

FIG. 5 is a plan view of the waist belt.

FIG. 6 is a cross section of the waist belt.

DETAILED DESCRIPTION

Figure 1:
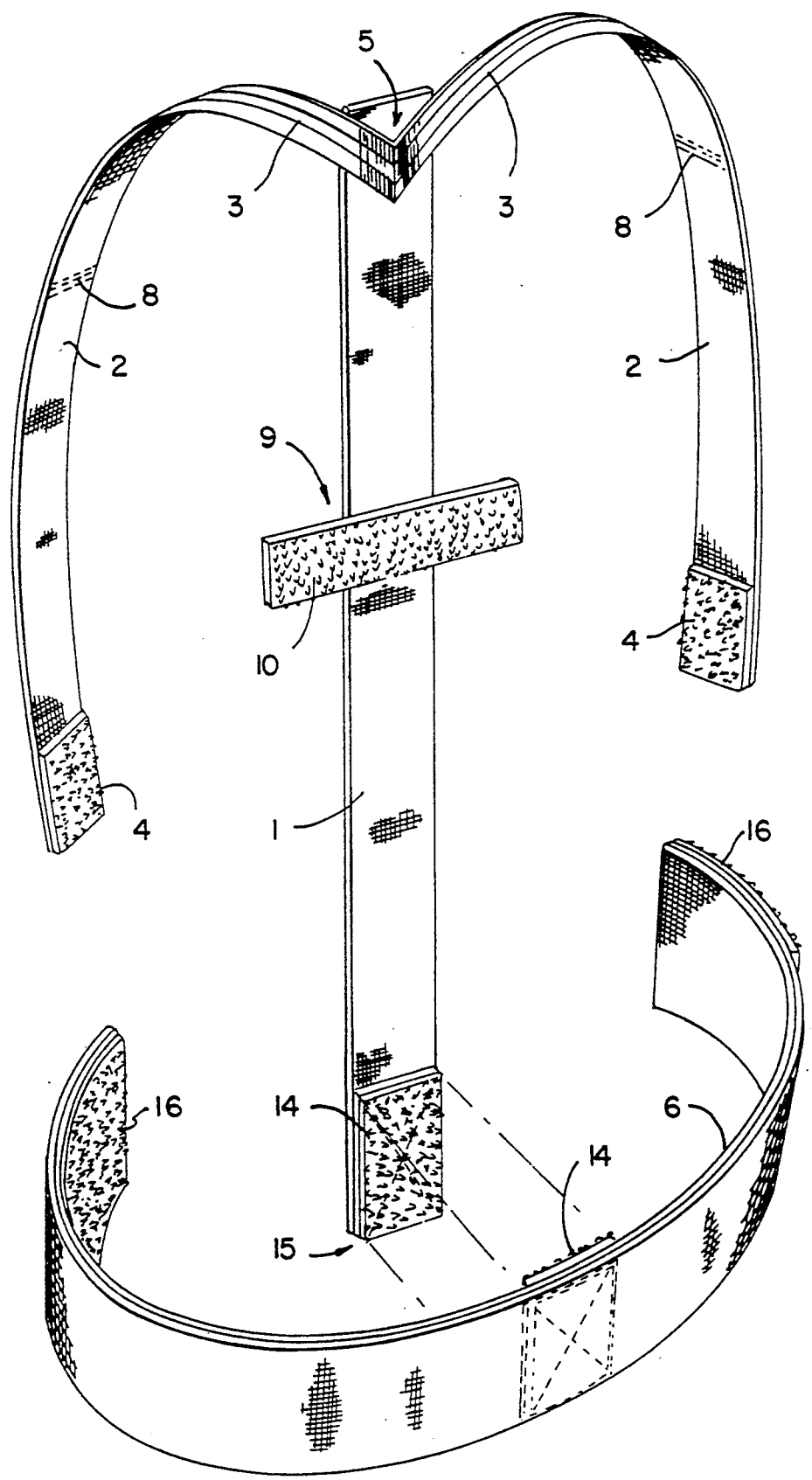
FIG. 1 is a perspective drawing of the basic embodiment of the brace.

FIG. 1 shows a perspective view of the posture correction and support device of the present invention comprising a first support means which rests against the spinal column as a back support strap 1. Attached to the top of the back support strap at 5 are two second support means which are adapted to fit over the shoulders and back under the arms as shoulder straps 2 which connect to the back support strap 1 at 9 by way of hook and loop fastener 4/10 such as, by way of example, VELCRO brand fasteners. Attached to the bottom of the back support strap 1 by way of a VELCRO fastener 14 is a third support means which fits around the waist as a waist belt 6.

Figure 2:
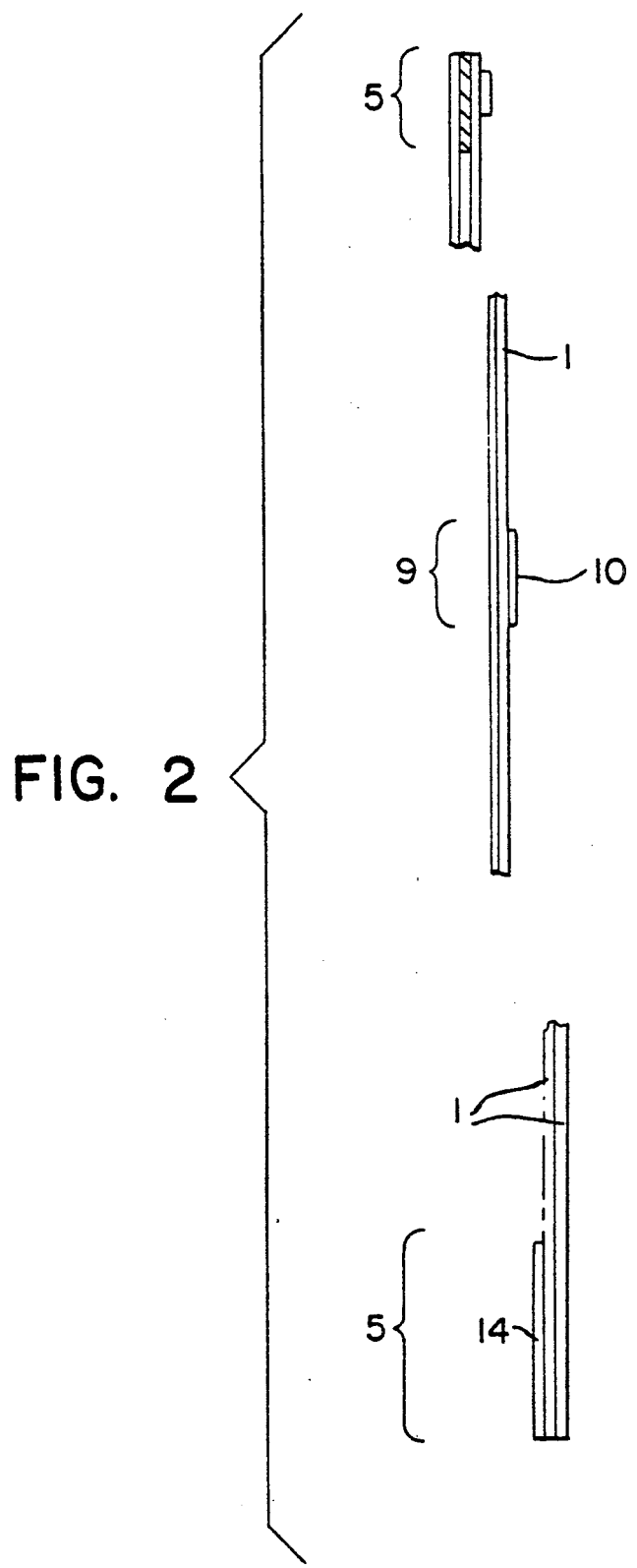
FIG. 2 is a cross section of the back support strap.

FIG. 2 shows a cross section of the back support strap 1 consisting of two layers of about 120% elastic about 50 mm wide laminated together at the top 5, middle 9 and bottom 15 to give an unextended length of about 450 mm. At about 160 mm down from the top of the back support strap 1, a length of VELCRO 10 about 230 mm long is attached across the outside of said back support strap, this point of attachment is referred to as point 9.

FIGS. 3 and 4 show plan and cross-section of the shoulder straps 2 consisting of a single layer of about 120% elastic about 50 mm wide. On the upper side of the shoulder strap 2 an elastic strip of about 25 mm wide 3 is sewn at either end and in the centre 8. The shoulder strap is attached to the top end of the back support strap 1 at point 5 to form a "V" joint. At the ends of the shoulder straps 2 a VELCRO strip 4 about 75 mm long is attached for adjustably connecting the shoulder straps to the back support strap at point 9 (see FIG. 4).

FIGS. 5 and 6 show plan and cross section-sections of the waist belt 6 consisting of a dual layer of about 120% elastic about 4" wide sewn together at either end whilst incorporating a VELCRO fastener 16. The centre of the dual belt is also sewn together whilst incorporating another VELCRO fastener 14 to facilitate attachment of the waist belt to the back support strap at point 15.

Figure 9:
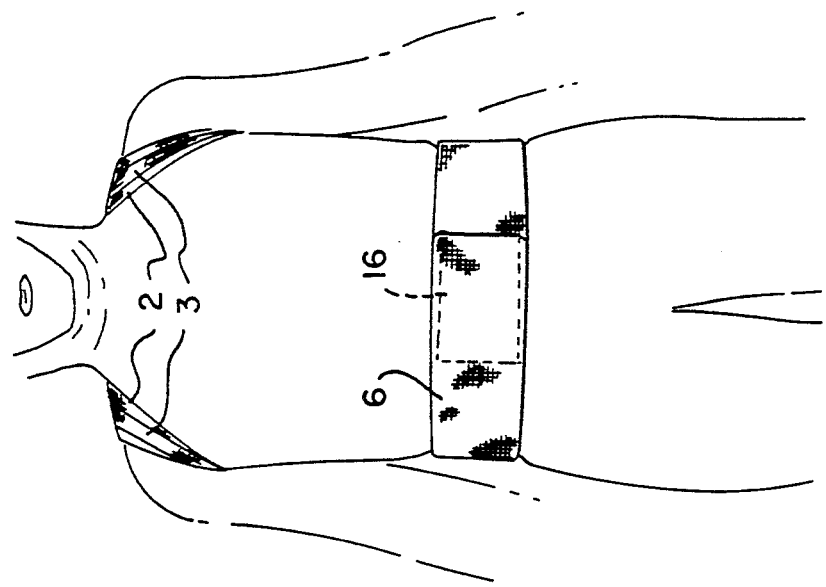
FIGS. 7, 8, 9, 10, 11 and 12 show the device being worn.
Figure 8:
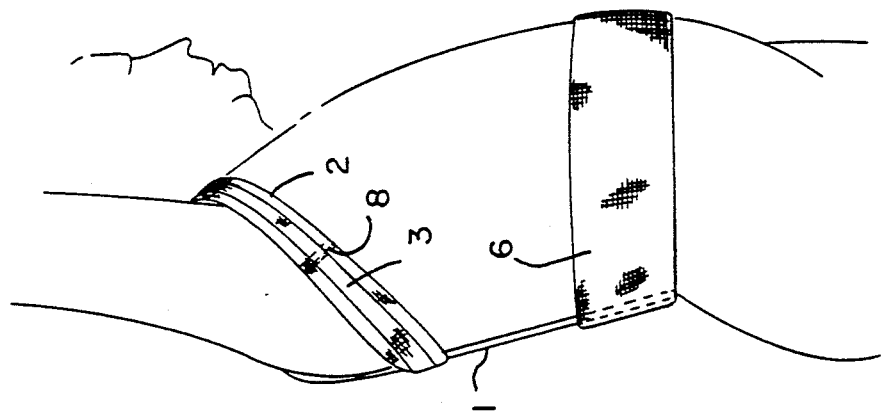
Figure 7:
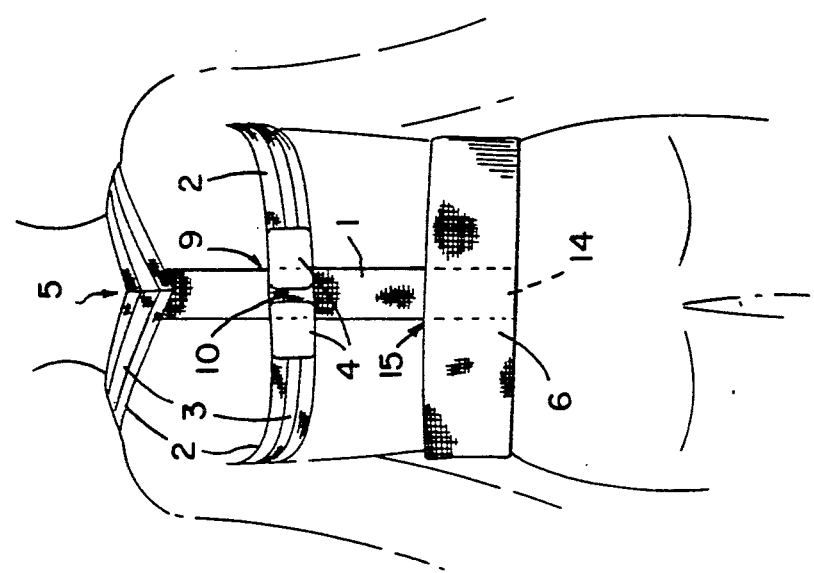

FIGS. 7, 8 and 9 show the device as fitted to a wearer.

Figure 12:
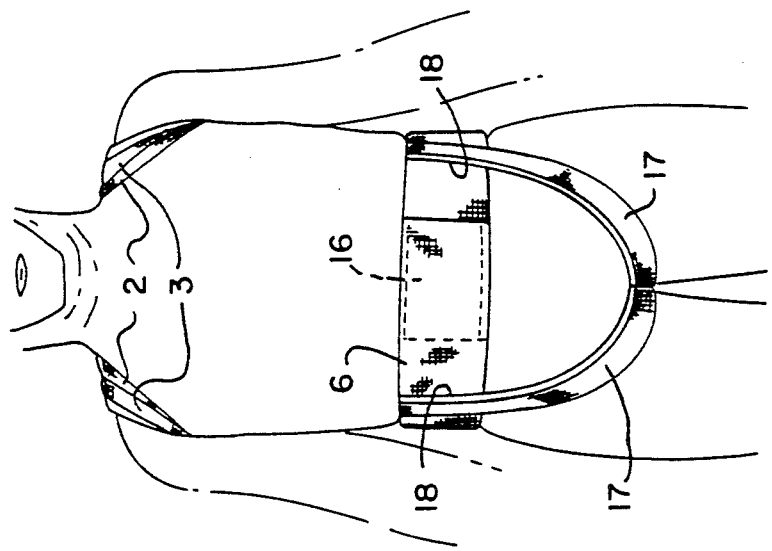
Figure 11:
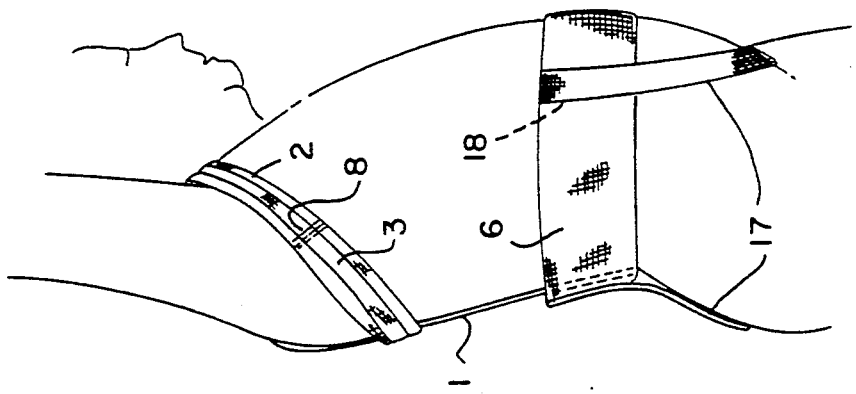
Figure 10:
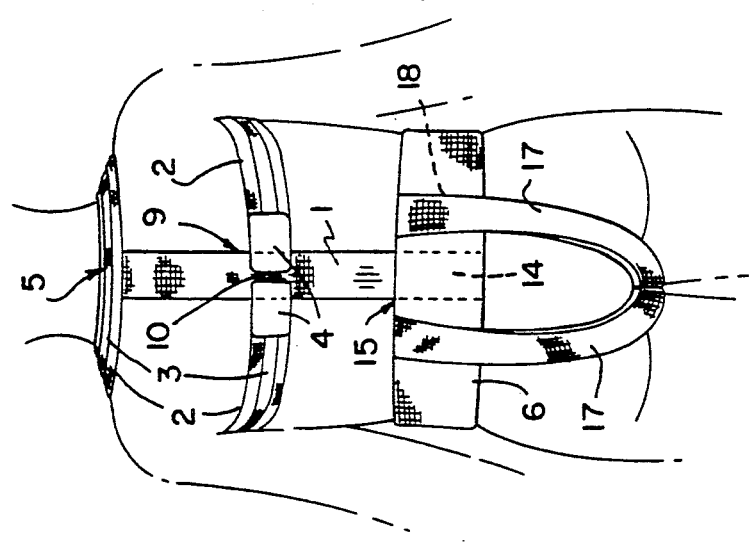

FIGS. 10, 11, and 12 show the device incorporating the optional pelvic anchor 17 as fitted to a wearer and the optional "T" joint of the first and second support means.

Figure 13:
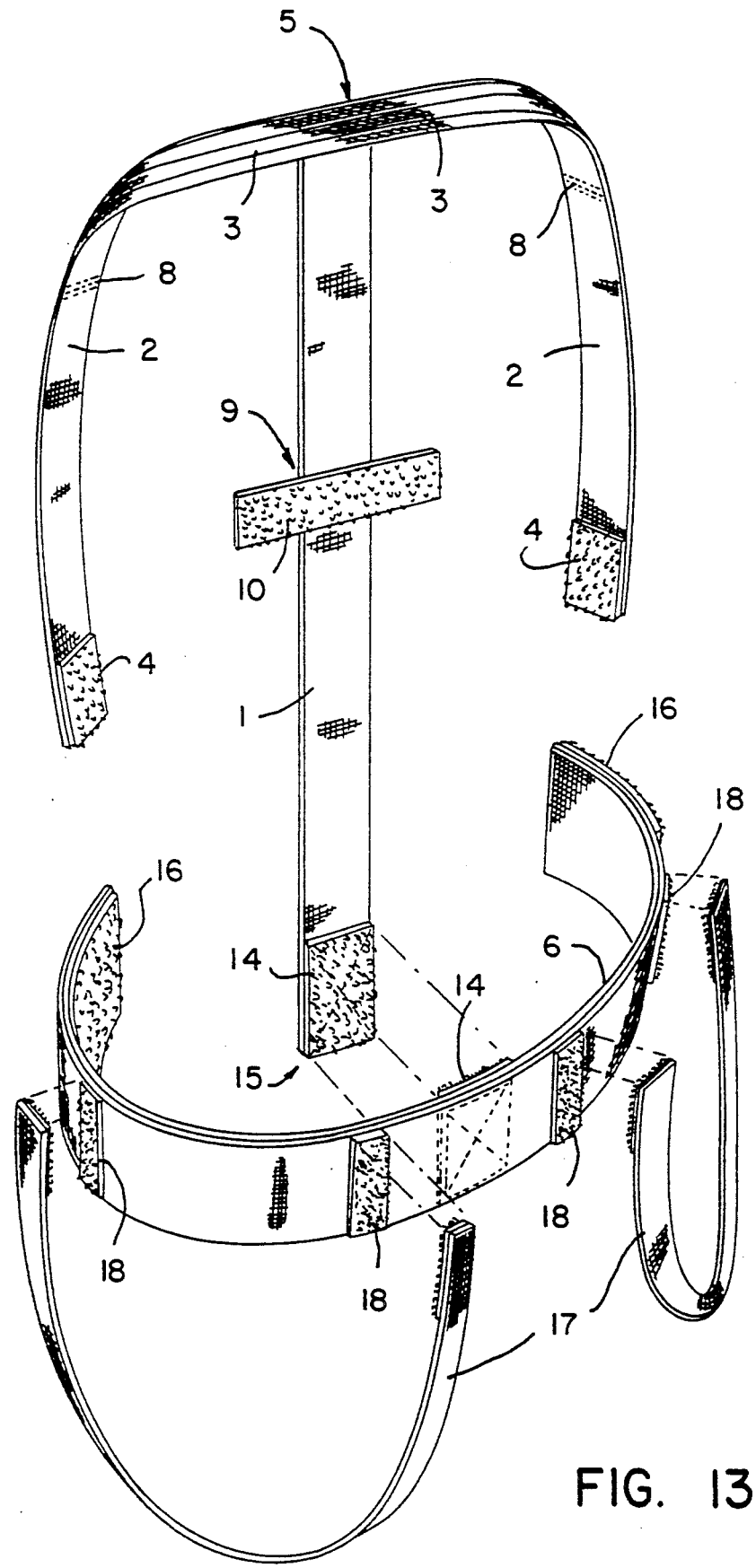
FIG. 13 shows a perspective view of the brace including pelvic anchors.

FIG. 13 shows a perspective view of the device incorporating the optional pelvic anchor and optional "T" joint of the first and second support means where anchors 17 are attached to the waist belt via a removable means.

Construction details of the preferred embodiment of the belt.

The belt may be made up of 3 fabricated parts.
a) The waist belt
b) The back support strap
c) The shoulder straps
d) The pelvic anchor (optional)

a) The Waist Belt

The belt is made from 100 mm elastic 2130 mm long 6.

The elastic is double so that both ends meet in the centre of the back of the belt.

A piece of elastic 14 approximately 100 mm ×100 mm is placed inside the joint and is all sewn together using a standard sewing pattern, such as that discussed below.

The sewing pattern will be the same in all cases unless stated, everything will be sewn in a rectangular pattern and also sewn diagonally both ways.

Over the joint in the belt a piece of 50 mm ×100 mm hard VELCRO 14 is sewn using the same sewing pattern.

At one end and on the same side as the hard VELCRO 16 over the joint a 100 mm ×160 mm piece of soft VELCRO 16 is sewn using the same sewing pattern.

On the other end of the belt and on the opposite side a 100 mm ×120 mm piece of hard VELCRO 16 is sewn using the same sewing pattern.

This completes the waist belt.

b) The Back Support Strap

The back support strap 1 is made from 50 mm elastic 1 1 meter long. One end is folded back by 200 mm, and the other end is folded until they meet. Both ends are sewn straight across to hold them together.

The piece of elastic is now doubled and 500 mm long.

A piece of 50 mm elastic 220 mm long and a piece of hard VELCRO 10 220 mm long are placed together with the rough side of the VELCRO facing inward and sewn across each end approximately 7 mm in.

It is then turned so that the rough side of the VELCRO is facing out and sewn using the same sewing pattern as for the waist belt.

This piece is placed across the joint on the back strap equally distanced 180 mm from the top of the back strap with the rough side of the VELCRO facing out and it is sewn using the same sewing pattern as for the waist belt.

On the same side as the rough VELCRO, approximately 320 mm from the top of the back strap, a piece of soft VELCRO 14 50 mm ×130 mm is sewn using the same pattern.

This completes the back strap.

c) The Shoulder Straps

The shoulder straps are made from one piece of 50 mm elastic 1350 mm 2 long and one piece of 25 mm elastic 1170 mm long.

To each end of the 50 mm elastic and on the same side a piece of soft VELCRO 50 mm ×110 mm is placed with the soft side facing inward. Each end is sewn straight across approximately 7 mm from the end. It is then turned to the correct side and sewn using the same sewing pattern as for the waist belt.

On the opposite side of this strap the 25 mm ×1170 mm strap is sewn. Without stretching this strap extended to a position in the centre of the 50 mm strap, with the end turned in by 10 mm it should position itself 15 mm into the area of the VELCRO but on the opposite side. Each end is sewn in a small rectangular pattern approximately 5 mm across.

From each end of the belt approximately 380 mm the straps are joined by 1 row of stitching to keep them together.

The shoulder straps are placed at the top between the back straps and centred (670 mm each way) with the 25 mm strap facing the same way as the rough VELCRO. It is then sewn using the same sewing pattern.

A piece of soft white material approximately 200 mm long and sewn in the form of a tube to slip loosely over each of the shoulder straps, although not part of the belt allows the belt to slide under the arms.

Each shoulder strap is then connected to the VELCRO cross piece on the back strap 10.

The 100 mm waist Belt is then attached to the VELCRO at the bottom of the back strap 14.

In operation, the posture correction device is assembled with the shoulder straps connected to the back support strap and the waist belt connected to the back support. The arms are then passed through the shoulder straps and the waist belt fastened around the waist approximately 3" above the natural waist line. The device is adjustable at two points, 9 and 15, such that the shoulder strap can be adjusted for length and position up or down the back support strap. The waist belt can also be adjusted for length and position up and down the back support strap.

d) The Pelvic Anchor

In addition the waist belt may incorporate two pelvic anchors 17 which slip under the crotch and prevent the belt from slipping up the waist region. The pelvic anchors may be made of inelastic or elastic strap attached to the waist belt with VELCRO type fastener 18 or other clips or buttons. Furthermore, the pelvic anchor aids in providing additional tension to the belt during frequent bending to assist in straightening the body after bending.

Details for wearing and adjusting the belt

The use of VELCRO is the method for adjusting the belt. This allows within the size range of the belt for a reasonable margin of adjustment.

The shoulder straps should be adjusted so that they do not feel tight when the belt is placed over the shoulders.

The bottom belt is set in a position where it is approximately 75 mm above the natural waist line. The minimum pressure should be set to give support with comfort, with the best anchoring at the pelvic region.

When the belt is pulled down into the waist's position it pulls the shoulders back and at the same time it helps the back into it's correct position. (The back has a natural "S" curve).

The front of the belt is usually pulled down towards the pit of the stomach.

The belt should sit just above the hips, as if you have it lower it can rub on this point.

When the belt is being worn close to the body, preferably over a singlet, it is recommended that the wearer use a liberal amount of a moisterising cream such as Vitamin E cream particularly around the waist and stomach area.

It is advisable to use a dry deodorant under the arms and a small quantity of Vitamin E or a similar product where the belt contacts the front of the shoulders.

The adjustment has to be determined by the wearer and it is recommended that in the first place it is done by a physiotherapist or an orthitist.

If the shoulder straps are lengthened then the waist belt may have to be raised up. If the shoulder straps are tightened the waist belt may have to be lowered to get the correct adjustment.

The thumbs can be slid under the front of the shoulder straps in the manner men used to stretch their braces in order to do the same with this belt, it allows adjustment of the pressure under the arms.

When the belt is adjusted and applied correctly there should only be a comfortable amount of pressure on the body. The pressure should only increase to support the movements of the body.

In addition, the belt supports the wearer when he bends over in fact in all movements.

When the wearer bends over, the elastic in the belt stretches and if the wearer relaxes he will feel the pressure of the belt wanting to return to its natural position. This action assists the person to straighten up.

At this stage it is advisable to tack both sides of the bottom belt at the point at top where it meets the back strap, 4 or 5 stitches at this point will prevent the bottom belt from peeling away when pulling it into place.

The belt can be worn over clothing if it is being used to support the back in a work situation.

IMPORTANT NOTICE

It is important to state that this belt has been designed specifically to help people suffering with ligamentious back problems.

The type of problem where the recommended treatment would be to assist the full extension of the body. Any other uses of the belt should only be under medical supervision.

The belt of the instant invention should not be used by people suffering from arthritis as the type of pressure applied can cause irritation of an arthritic condition.

Once fitted and adjusted, the device shall exert a multitude of forces to the back and shoulder region. Principally the shoulder straps serve to pull the shoulders back and prevent slumping whilst giving an anchorage point for the back support strap.

The waist belt serves to pull the lumbar region in, and by virtue of its attachment to the back support strap, also up. The combined force of pulling the lumbar region in and up serves to correct a very common back and posture problem.

In fact, evidence suggests that the correct orientation of the lumbar region has a very influential effect on the whole spine such that a vast range of spinal disorders are remedied by correction of the lumbar region.

Although not wishing to be bound to a particular mode of action, the instant device appears to have a direct influence on the spinal column by pushing the vertebrae into alignment whilst also functioning as a compliant restraint which serves to exercise the muscles of the back and back to naturally align the spine.

As can be seen by the foregoing, the device of the present invention provides a unique combination of forces in both dorso-vertical and vertical planes which serve correct posture and spinal alignment. The device is of simple construction, easy to adjust and comfortable to wear allowing full movement whilst maintaining the correcting tension on the back and shoulders.

What I claim is:

1. A posture correction and support device consisting essentially of: a first, single elongated, elastic, flexible support means adapted to lie along and be disposed in alignment with the spinal column from the cervical region to the lumbar region when said device is placed on the body, said support means being extensible in the direction of elongation to form an elastic and compliant spinal column support for providing continuous support and alignment of the spine during all stages of body movement; a second support means extending laterally outwardly from and connected to the top of said first support means and adapted to fit over the shoulder, under the arm and connect back to said first support means, and a third support means detachably connected to the bottom of said first support means and adapted to fit around the waist.

2. A posture correction and support device according to claim 1 wherein the second support means are a matching pair adapted to fit over either shoulder, under the arms and connect together at about the thoracic region of the first support means.

3. A posture correction and support device according to claim 1 wherein said second and third support means are elastic straps with adjustable connection means.

4. A posture correction and support device according to claim 3 wherein the elastic strap comprising the first and second support means is about 2" wide and the elastic strap comprising third support means is about 4" wide.

5. A posture correction and support device according to claim 3 wherein the first support means comprises a dual laminated strip of 2" elastic stretchably joined together, the second support means comprises a dual lamination of a 2" and a 1" strip of elastic stretchably joined together and the third support means comprises a dual laminated strip of 4" elastic.

6. A posture correction and support device according to claim 5 wherein the first support means comprises 120% elastic joined together at either end and in the centre and having an unextended length of about 450 mm, the second support means comprises 120% elastic joined together at either end and in the centre, the third support means comprises 120% elastic joined together at either end and in the centre and wherein the adjustable connection means are hook-and-loop type fasteners.

7. A posture correction and support device according to claim 2 wherein said support means are elastic straps with adjustable connection means.

* * * * *